United States Patent [19]

Cort

[11] B 3,986,980

[45] Oct. 19, 1976

[54] SYNERGISTIC ANTIOXIDANT COMPOSITION COMPRISING ASCORBIC ACID AND 6-HYDROXY-2,5,7,8-TETRAMETHYLCHROMAN-2- CARBOXYLIC ACID

[75] Inventor: Winifred Cort, Little Falls, N.J.

[73] Assignee: Hoffmann-La Roche Inc., Nutley, N.J.

[22] Filed: Apr. 17, 1975

[21] Appl. No.: 569,125

[44] Published under the second Trial Voluntary Protest Program on February 24, 1976 as document No. B 569,125.

Related U.S. Application Data

[62] Division of Ser. No. 465,217, April 29, 1974, Pat. No. 3,803,317.

[52] U.S. Cl. .................... 252/404; 426/545; 426/546; 426/610; 252/407

[51] Int. Cl.² .................... A23D 5/04; C09K 15/06; C07D 259/00

[58] Field of Search .......... 426/268, 544, 545, 546, 426/610, 323, 541; 260/345.5, 398.5; 252/404, 407

[56] References Cited

UNITED STATES PATENTS

| | | | |
|---|---|---|---|
| 2,511,428 | 6/1950 | Buxton | 426/228 |
| 3,313,826 | 4/1967 | Gale | 426/228 |
| 3,364,234 | 1/1968 | Schoenewaldt | 426/328 |
| 3,502,594 | 3/1970 | Ahrens | 260/398.5 |

FOREIGN PATENTS OR APPLICATIONS

| | | | |
|---|---|---|---|
| 45-29413 | 9/1970 | Japan | 426/183 |
| 949,715 | 2/1964 | United Kingdom | 260/345.5 |

*Primary Examiner*—Norman Yudkoff
*Assistant Examiner*—Curtis P. Ribando
*Attorney, Agent, or Firm*—Samuel L. Welt; Bernard S. Leon; R. Hain Swope

[57] ABSTRACT

Synergistic antioxidant compositions useful as additives for edible fats and oils comprising ascorbic acid and rac. 6-hydroxy-2,5,7,8-tetramethylchroman-2-carboxylic acid are described.

2 Claims, No Drawings

SYNERGISTIC ANTIOXIDANT COMPOSITION COMPRISING ASCORBIC ACID AND 6-HYDROXY-2,5,7,8-TETRAMETHYLCHROMAN-2- CARBOXYLIC ACID

This is a division, of application Ser. No. 465,217, filed Apr. 29, 1974, now U.S. Pat. No. 3,803,317.

BACKGROUND OF THE INVENTION

The present invention pertains to antioxidant compositions which are useful in the preservation of edible fats and oils. It is well known that certain edible fats and oils such as, for example, lard, peanut oil, cottonseed oil, corn oil and the like are deficient in natural antioxidants. Due to this deficiency, such products are highly vulnerable to deterioration in the presence of oxygen or air and will become rancid upon storage, thereby becoming discolored and developing unpleasant odors and flavors.

The present invention is predicated on the discovery that certain combinations of ascorbic acid and rac. 6-hydroxy-2,5,7,8-tetramethylchroman-2-carboxylic acid produce a synergistic antioxidant effect and are especially useful as the antioxidant component for compositions comprising in whole or part edible fats and oils.

DETAILED DESCRIPTION OF THE INVENTION

The present invention is directed to synergistic antioxidant compositions comprising mixtures of ascorbic acid and rac. 6-hydroxy-2,5,7,8-tetramethylchroman-2-carboxylic acid. More particularly, the present invention is directed to compositions comprising from about one part to about twenty parts by weight ascorbic acid for each part by weight of rac. 6-hydroxy-2,5,7,8-tetramethylchroman-2-carboxylic acid. More preferred compositions in accordance with the present invention comprise from about one part by weight to about ten parts by weight ascorbic acid for each part by weight of rac. 6-hydroxy-2,5,7,8-tetramethylchroman-2-carboxylic acid. Especially preferred in accordance with the present invention are compositions comprising two and one-half parts by weight ascorbic acid for each part by weight rac. 6-hydroxy-2,5,7,8-tetramethylchroman-2-carboxylic acid.

The synergistic antioxidant combination of the present invention is particularly useful in the stabilization of edible fats and oils in that they are nontoxic, functional in fats and oils and free of undesirable orders, flavors and colors when incorporated in such substances in the amounts contemplated herein. Examples of edible fats and oils include lard, soy bean oil, cod-liver oil, corn oil, cottonseed oil, fish oil, safflower oil, rice oil, peanut oil, castor oil and the like. The effectiveness of the compositions of the invention in soy bean oil is of commercial significance since sales of soy bean oil constitutes about 60% of the total sales of all edible fats and oils. The compositions of the invention are likewise effective in stabilizing agsinst oxidation those foods which contain a high percentage of oils or fats such as, for example butter, margarine, cheese, mayonnaise, prepared salad dressings, potato chips, sausages and the like.

To effectively inhibit oxidation in the above materials, mixtures of ascorbic acid and rac. 6-hydroxy-2,5,7,8-tetramethyl-chroman-2-carboxylic acid in the precentages given above are added thereto in from about 0.01 percent by weight to about 1.0 percent by weight, perferably from about 0.02 percent by weight to about 0.2 percent by weight. These percent by weight ranges will vary somewhat according to the substance to be protected as is recognized in the art.

The synergistic antioxidant compositions of the present invention are admixed with the substance to be protected by methods commonly recognized in the art of food chemistry. The combination of the present invention has been found to be superior in effect to known antioxidants and combinations of antioxidants used with the same materials as indicated above. The antioxidant combination of this invention is prepared by simple admixture of the active compounds. Rac. 6-hydroxy-2,5,7,8-tetramethylchroman-2-carboxylic acid can be prepared according to the following examples.

EXAMPLE 1

A solution of 2.4 g. (0.1 mol.) of rac. 6-acetoxy-2-hydroxy-2.5,7,8-tetramethylchroman in a total of 200 ml. of dimethyl-sulfoxide was rapidly stirred as 32.5 g. (0.5 mol.) of granular KCN was added thereto by sifting so that a uniformly dispersed suspension was obtained. The resulting suspension was cooled to 15° centigrade as 47.0 ml of 12N aqueous $H_2SO_4$ was added over 1.25 hrs. as the internal temp. was maintained at 20 degrees centigrade. Tlc at this point showed a major, slowerrunning spot in addition to trace of starting material. The material was poured into diethylether and $H_2O$. The ether soulutions were washed with water and brine, dried over $NaSO_4$ and stripped of solvent to yield rac. 2-cyano-4-(5-acetoxy-2-hydroxy-3,4,6,-trimethylphenyl)-butan-2-ol as a gum.

EXAMPLE 2

The cyanohydrin prepared in Example 1 was immediately taken up in 250 ml of methanol. This solution was cooled in an ice bath, saturated with anhydrous hydrochloric acid, stored for 18 hours at −2°C and stripped of solvent on a rotary evaporator (bath temp less than 30°C). The resulting gum was taken up in 250 ml of water, degassed, placed under nitrogen and heated for 2.0 hours at 40°C to produce an aqueous suspension. The aqueous suspension was worked up and dried utilizing a solvent mixture of ethyl acetate and diethyl ether to produce a mixture containing rac. 2-carbomethoxy-4-(2,5-hydroxy-3,5,6-trimethylphenyl)-butan-2-ol and rac. 2-carbomethoxy-6-hydroxy-2,5,7,8-tetramethyl-chroman. This mixture was a tan solid. The tan solid was triturated with diethyl ether and then crystallized from diethyl ether to give rac. 2-carbomethoxy-4-(2,5-hydroxy-3,5,6-trimethylphenyl)-butan-2-ol as white prisms: pm 135°–136.5°C.

From the aqueous suspension prepared above, the ester rac. 2-carbomethoxy-6-hydroxy-2,5,7,8-tetramethylchroman was isolated by filtration of the aqueous suspension prior to working up.

EXAMPLE 3

The tan solid of Example 2 was suspended in 100 ml. of 2N aqueous NaOH. The resulting solution was stirred under $N_2$ for 24 hours, treated with 57 ml of 2N aqueous HCl followed by 10 ml of staurated aqueous $NaHCO_3$ solution to give a solution of pH 7.5–8.0. The solution was extracted with diethyl ether, acidified with 2N aqueous HCl and again extracted with diethyl ether. These latter extracts were washed with brine, dried ($Na_2SO_4$) and stripped of solvent. The resulting 24.3 g of gum which partially crystallized was shown by tlc to be an approximately equimolar mixture of cyclized and uncyclized acids. Pure uncyclized acid, rac. 2-carboxy-4-(2,5-dihydroxy-3,4,6-trimethyl)-butan-2-ol was isolated from this mixture by filtration of the aqueous suspension obtained upon acidification, extraction with diethyl ether and crystallization from diethyl ether, as a white solid which was very susceptible to air oxidation: mp 177°–178°C.

EXAMPLE 4

The crude mixture of acids in Example 3 and 0.57 g of p-toluenesulfonic acid monohydrated in 300 ml of benzene was heated at reflux under $N_2$ with azeotropic removal of $H_2O$ for 1.25 hr. The cooled solution was washed with a total of 300 ml of one-half saturated aqueous $NaHCO_3$ and with brine. The aqueous solutions were treated with charcoal, acidified with 2N aqueous HCl and filtered to give rac. 6-hydroxy-2,5,7,8-tetramethylchroman 2-yl carboxylic acid as a light tan powder, mp, 189°–190°C.

EXAMPLE 5

Rac. 6-hydroxy-2,5,7,8-tetramethylchroman-2-carboxylic acid alone and in combination with several other substances prosessing antioxidant activity was tested by means of the Swift Stability Test, commonly referred to as the Active Oxygen Method (AOM). This test, which is described in Official and Tentative Methods, American Oil Chemists Society, Vol. 1, A.O.C.S. Champaign, Ill. (1964), consists in general of bubbling air through a sample until rancidity develops. The AOM time in hours as expressed in the following table represents hours required to reach 70 P.V., i.e. 70 meg. peroxides at 98°C. The data in Table I represents tests in soybean oil. For comparative purposes the value of each component is shown alone. All percents are percents by weight.

Table I

| Additive | Hours to reach 70 P.V. Alone | Plus 0.02% rac. 6-hydroxy-2,5,7,8-tetramethyl-chroman-2-carboxylic acid |
|---|---|---|
| None | 5 | 27 |
| 0.02% Ascorbyl Palmitate | 11 | 35 |
| 0.02% Ascorbyl Palmitate +0.02% Thiodipropionic acid | 30 | 69 |
| 0.2% Ascorbyl Palmitate | 27 | 47 |
| 0.2% Ascorbyl Palmitate +0.02% Thiodipropionic | 67 | 98 |
| 0.2% Ascorbic Acid | 150 | 190 |

The 190 hour value for the combination of 0.2% ascorbic acid and 0.02% rac. 6-hydroxy-2,5,7,8-tetramethylchroman-2-carboxylic acid is considered exceptional.

In Table II, the activity of the combination of ascorbic acid and rac. 6-hydroxy-2,5,7,8-tetramethylchroman-2-carboxylic acid was compared against a number of antioxidant materials commonly utilized to stabilize edible fats and oils. Experiments were conducted with olive oil which contained 20mg% total tocopherol (16mg% alpha and 4mg% gamma) and "stripped" safflower oil. The latter was prepared on a rotary molecular still at 270° under vacuum to remove tocopherols.

Table II

| Additive | Hours to reach 70 P.V. "Stripped" Safflower Oil | Olive Oil |
|---|---|---|
| None | 1 | 6 |
| 0.02% Butylated Hydroxytoluene (BHT) | 5 | 14 |
| 0.02% Butylated Hydroxyanisole (BHA) | 4 | 9 |
| 0.02% Propyl Gallate | 6.4 | 11 |
| 0.02% Alpha - Tocopherol | 4 | 6 |
| 0.02% Gamma - Tocopherol | 4 | 8 |
| 0.02% Tertiary Butyl Hydroquinone (TBHQ) | 9.5 | 8.0 |
| 0.02% rac. 6-hydroxy-2,5,7,8-tetramethylchroman-2-carboxylic acid | 20 | 55 |

In Table III the synergistic antioxidant activity of rac. 6-hydroxy-2,5,7,8-tetramethylchroman-2-carboxylic acid in combination with ascorbic acid was clearly demonstrated by showing the activity combinations of rac. 6-hydroxy-2,5,7,8-tetramethylchroman-2-carboxylic acid and other commonly used antioxidants at their recognized effective levels. This experiment was run in soybean oil at 98°C.

Table III

| Additive | Hours to reach 70 P.V. |
|---|---|
| None | 5 |
| 0.02% Rac. 6-hydroxy-2,5,7,8-tetramethylchroman-2-carboxylic acid | 27 |
| 0.02% Rac. 6-hydroxy-2,5,7,8-tetramethylchroman-2-carboxylic acid + 0.02% BHA | 28 |
| 0.02% Rac. 6-hydroxy-2,5,7,8-tetramethylchroman-2-carboxylic acid + 0.02% BHT | 28 |
| 0.02% Rac. 6-hydroxy-2,5,7,8-tetramethylchroman-2-carboxylic acid +0.02% Ascorbyl Palmitate | 34 |
| 0.02% Rac. 6-hydroxy-2,5,7,8-tetramethylchroman-2-carboxylic acid +0.02% Propyl Gallate | 34 |
| 0.02% Rac. 6-hydroxy-2,5,7,8-tetramethyclchroman-2-carboxylic acid +0.02% TDPA | 41 |
| 0.02% Rac. 60hydroxy-2,5,7,8-tetramethylchroman-2-carboxylic acid +0.02% TBHQ | 47 |
| 0.02% Rac. 6-hydroxy-2,5,7,8-tetramethylchroman-2-carboxylic acid +0.02% Ethylenediaminetetra acetic acid | 26 |
| 0.02% Rac. 6-hydroxy-2,5,7,8-tetramethylchroman-2-carboxylic acid +0.2% Ascorbyl Palmitate | 45 |
| 0.02% Rac. 6-hydroxy-2,5,7,8-tetramethylchroman-2-carboxylic acid +0.02% Ascorbyl Palmitate +0.02% TDPA | 69 |
| 0.02% Rac. 6-hydroxy-2,5,7,8-tetramethylchroman-2-carboxylic acid +0,2% Ascorbic acid | 200 |

In Table IV, the synergistic antioxidant activity of combinations of rac. 6-hydroxy-2,5,7,8-tetramethylchroman-2-carboxylic acid and ascorbic acid was again demonstrated in comparison with several known antioxidants utilizing as substrates a number of commonly used oils.

Table IV

| Additive | Hours to reach 70 P.V. Corn Oil | Cottonseed Oil | Peanut Oil | Lard |
|---|---|---|---|---|
| None | 13 | 11 | 12 | 3 |
| 0.02% BHT | 14 | 15 | 22 | 30 |
| 0.02% BHA | 13 | 15 | 13 | 45 |

Table IV-continued

| Additive | Hours to reach 70 P.V. | | | |
|---|---|---|---|---|
| | Corn Oil | Cottonseed Oil | Peanut Oil | Lard |
| 0.02% Propyl Gallate | 26 | 21 | 36 | 70 |
| 0.02% TBHQ | 34 | 38 | 52 | 42 |
| 0.02% Rac.6-hydroxy-2,5,7,8-tetramethyl-chroman-2-carboxylic acid | 28 | 36 | 36 | 73 |
| 0.02% Rac. 6-hydroxy-2,5,7,8-tetramethyl-chroman-2-carboxylic acid +0.05% Ascorbic Acid | 90 | 45 | 164 | 150 |
| 0.02% Rac.6-hydroxy-2,5,7,8-tetramethyl-chroman-2-carboxylic acid +0.01 Ascorbic Acid | 96 | 66 | 170 | 200 |

I claim:

1. A synergistic antioxidant composition consisting essentially of from about one part by weight to about 20 parts by weight of ascorbic acid per part by weight of rac. 6-hydroxy-2,5,7,8-tetramethylchroman-2-carboxylic acid.

2. The composition of claim 1 which consists essentially of 2.5 parts by weight ascorbic acid per part by weight rac. 6-hydroxy-2,5,7,8-tetramethylchroman-2-carboxylic acid.

* * * * *